(12) United States Patent
Lee et al.

(10) Patent No.: US 7,667,848 B2
(45) Date of Patent: Feb. 23, 2010

(54) IMAGING APPARATUS FOR INFRARED RAYS NONLINEAR MOLECULAR VIBRATIONAL MICROSCOPY

(75) Inventors: Jae Yong Lee, Chungbuk (KR); Eun Seong Lee, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 0 days.

(21) Appl. No.: 11/861,987

(22) Filed: Sep. 26, 2007

(65) Prior Publication Data
US 2008/0304046 A1 Dec. 11, 2008

(30) Foreign Application Priority Data
Jun. 8, 2007 (KR) .................... 10-2007-0055952

(51) Int. Cl.
*G01J 3/45* (2006.01)

(52) U.S. Cl. .................................................. 356/451
(58) Field of Classification Search ................ 356/451, 356/456, 301, 502; 250/339.07, 339.09
See application file for complete search history.

(56) References Cited

U.S. PATENT DOCUMENTS

| | | | | |
|---|---|---|---|---|
| 6,809,814 B2* | 10/2004 | Xie et al. | ..................... | 356/301 |
| 7,075,658 B2* | 7/2006 | Izatt et al. | ................... | 356/479 |
| 7,388,668 B2* | 6/2008 | Potma et al. | ................ | 356/451 |
| 2004/0207850 A1* | 10/2004 | Kwak et al. | ................. | 356/432 |
| 2005/0280827 A1* | 12/2005 | Potma et al. | ................ | 356/485 |
| 2006/0238745 A1* | 10/2006 | Hashimoto et al. | ............ | 356/73 |
| 2007/0088219 A1* | 4/2007 | Xie et al. | .................... | 600/473 |

* cited by examiner

*Primary Examiner*—Tarifur Chowdhury
*Assistant Examiner*—Jonathan M Hansen
(74) *Attorney, Agent, or Firm*—The Webb Law Firm

(57) ABSTRACT

Disclosed is an imaging apparatus for infrared nonlinear molecular vibrational microscopy.

2 Claims, 6 Drawing Sheets

IMAGING APPARATUS FOR INFRARED RAYS NONLINEAR MOLECULAR VIBRATIONAL MICROSCOPY

TECHNICAL FIELD

The present invention relates to an infrared rays nonlinear molecular vibrational spectroscopic microscope and a method thereof, more particularly, to a technology for obtaining a molecular vibrational microscopic image using a nonlinear spectroscopic signal obtained by focusing and spatial scanning of multi-wavelength laser beams in a sample.

BACKGROUND ART

In observing an optically transparent micro-sample including a bio-sample like cells and tissues under a general optical microscope, there are some problems that it is very difficult to obtain a clear morphological image of various intracellular organs and materials in the sample and also it is impossible to selectively measure a spatial distribution of molecular chemical species. This is because a difference between objects and a background substance is minute in optical properties and thus a sufficient optical contrast therebetween is not provided. In other words, it is not easy to distinguish the specific micro-structures or micro-materials to be observed from the background substance in the sample.

To explore phenomena of life science and disease mechanisms by observing behavior of intracellular organs or metabolites in cells through optical images, a laser scanning fluorescent microscope which could overcome a limitation of a general optical microscope has been widely used for a long time. According to an operation principle of the laser scanning fluorescent microscope, the sample is dyed with a fluorescent marker which selectively combines with the objects to be observed, and then fluorescence generated by scanning ultraviolet or visible laser irradiation is detected spatially, thereby obtaining an optical image in which the objects gain high contrast selectively. However, since the fluorescent marker as an exogenous material is added in the bio-sample, there is a basic problem that an original status of the bio-sample is not maintained as it was. Because the added exogenous material lowers activity of the bio-sample, it is difficult to obtain exact information about the behavior of the bio material. Furthermore, since a coloring matter of the fluorescent marker is easily photobleached even by very weak lasers, it is also difficult to observe the image continuously or in time-lapse measurements.

In order to avoid the disadvantages of the laser scanning fluorescent microscope, there has been proposed a new microscopic technology which can detect a spectroscopic characteristic of a material itself without the fluorescent marker which is selectively combined with molecules of the material and thus obtain a molecular image. As a representative method of analyzing spectroscopic signals of its own molecular vibrational fingerprint generated by interaction between particular molecules and laser beams, there are infrared absorption spectroscopy and Raman scattering spectroscopy which are combined with a microscopic optical system so as to be used for molecular image measurement of a microstructure.

FIG. 1 is a diagram of a molecular vibrational transition showing the principle of measuring an infrared absorption spectroscopic signal.

An infrared absorption microscope uses the principle that, when a laser beam scanned in a sample has a wavelength which resonates with inherent molecular vibration, the laser beam is strongly absorbed by the sample, and the intensity of the laser which is transmitted or reflected is reduced. The infrared absorption molecular image is obtained by measuring an attenuation ratio of the laser as a function of wavelength with respect to a scanning position of the laser beam.

FIG. 2 is a diagram of a molecular vibrational transition showing the principle of generating a spontaneous Raman spectroscopic signal.

In a Raman microscope, pixel data constructing a molecular image is formed by a spontaneous Raman spectrum generated by scanning the laser of a predetermined wavelength on the sample. Unlike in the infrared absorption microscope, a red-shifted Raman spectroscopic signal is generated by inelastic scattering of photons of the laser having a fixed wavelength which does not resonate with the molecular vibration of the objects. In this case, energy difference between incident photons and Raman-scattered photons corresponds to molecular vibration mode energy of materials in the sample. In other words, the Ramna spectrum obtained by collecting the laser beam scattered by the sample includes information about the inherent molecular vibration mode of the materials constituting the sample.

The infrared absorption microscope and the Raman microscope have various advantages and disadvantages, respectively.

Since the infrared absorption microscope is based on a linear absorption phenomenon, it is very simple to understand the principle and to analyze the signal. Furthermore, since the infrared absorption microscope uses a direct absorption spectroscopic signal generated from the resonance of the excitation laser and the molecular vibration mode, it offers high sensitivity and signal-to-noise ratio in the measurement. However, in the mid-IR regime with wavelength range of 2.5~18 µm where light is resonated with the molecular vibration and thus strongly absorbed, it is in practice very difficult to realize a wavelength-tunable laser beam source which is required for the microscopic image. Furthermore, due to the limitation imposed by diffraction phenomenon, the infrared absorption microscope has a very low spatial resolution of 10~40 µm compared with the spatial resolution (of 0.3~0.5 µm) in an optical microscope with a visible beam source. To solve the problem of lacking tunable mid-IR sources, a wavelength dispersive detector or an interferometer for fourier-transform spectroscopy is employed in the measuring part, in order for a white beam source having a wide spectrum from the visible to the mid-IR to be used.

On the contrary, since the Raman microscope uses a single wavelength beam source not related to a molecular vibrational frequency, the excitation laser is given less weight in constructing the Raman microscope, and its operation is very simple. Furthermore, since the Raman microscope uses a laser source having a short wavelength of the visible light range, it has an advantage of obtaining the microscopic image having a good spatial resolution. However, it has also a disadvantage that it takes a long time to obtain an image because the intensity of Raman signal for providing spectroscopic information is very weak. Particularly, in the case that a dynamic characteristic of the living bio-sample is observed, or an intensity of excitation laser cannot be sufficiently increased to avoid damage to the sample, the disadvantage becomes further serious.

Research and development has been carried out continuously to overcome the above disadvantages of the infrared absorption microscope and the Raman microscope.

In order to improve the low spatial resolution of the infrared absorption microscope, there has been proposed a scanning near-field IR microscope using metal-coated optical fiber in which an aperture of a few hundred nm is formed at a distal end of a tip. Herein, the spatial resolution does not depend on the IR diffraction limitation, but depends on the size of aperture formed at the tip of the optical fiber, regardless of the wavelength of a laser beam, thereby providing the spatial resolution comparable with that in the optical microscope using a visible beam source. However, in order to obtain the microscopic image, it is necessary for a surface of the sample to be mechanically scanned with high precision relative to the tips of the optical fiber, but it is difficult to quickly obtain the image since the aperture has a very low transmission efficiency ($\sim 10^{-6}$) at IR wavelengths. In addition, with a current technical standard, it is difficult to provide a reliable process technology which manufactures the optical fiber for efficiently transferring the IR. That is, it overcomes the limitation of the spatial resolution, whereas it submits to a sacrifice of the measurement sensitivity and the speed for obtaining the microscopic image.

A coherent anti-Stokes Raman scattering (CARS) microscope overcomes substantially low sensitivity and slow speed for obtaining the microscopic image which were critical disadvantages in the conventional Raman microscope. In detecting of molecular vibrations, CARS is also based on the Raman scattering phenomenon is similar to that in the conventional Raman microscope. However, the fundamental difference is not to use the spontaneous Raman scattering as a linear optical phenomenon, but to use a four wave mixing in which three incident laser beams are interacting with the sample so as to generate a nonlinear optical signal.

FIG. 3 is a diagram of a molecular vibrational shift showing a principle of generating a CARS nonlinear spectroscopic signal.

Referring to FIG. 3, two incident laser beams (pump beam and Stokes beam) having a frequency difference corresponding to Raman shift of a certain molecule in the sample generate a beat and then induces forced harmonic molecular vibration which is coherent with the beat waveform. If a third laser beam (probe beam) is incident on the molecules which are vibrating in phase with coherence a status that phases are harmonized, anti-Stokes Raman scattering whose wavelength becomes shorter takes place through interaction, resulting in a coherent signal beam having the same phase in a predetermined propagating direction. Then, the nonlinear optical signal is precisely mapped in a space of the sample, thereby obtaining the CARS microscopic image.

The CARS microscope has an advantage of providing a very high measurement sensitivity and high speed for obtaining the image as well as obtaining the selective image. Since the CARS generates a very intense signal beam than the spontaneous Raman scattering, it is possible to quickly obtain high quality images having a good signal-to-noise ratio. The CARS phenomenon depends on the characteristic of third-order nonlinear optical susceptibility inherent to a material that give rise to four wave mixing, and therefore provides a signal enhancement proportional to the cube of incident laser beam intensity, and also provides a mechanism of obtaining a three-dimensional image of an inner portion of the sample with a high spatial resolution, as in laser confocal microscopes. Moreover, since the CARS phenomenon is an optical parametric conversion process which does not dissipate any laser energy in the measured sample after the interaction, it is a non-invasive measuring method which can avoid thermal damage to the sample by the laser.

However, the CARS microscope has also some disadvantages that the molecular selectivity and the signal-to-noise ratio are lowered by the non-resonant third-order nonlinear optical susceptibility which is not relevant to the natural vibration of molecules, and the measurement sensitivity is still low in comparison with a method using direct resonance absorption in the mid-IR range.

DISCLOSURE OF THE INVENTION

It is an object of the present invention to provide an imaging apparatus for infrared rays nonlinear molecular vibrational microscopy, which uses molecular vibrational resonance of IR laser and overcomes the problem that the spatial resolution is seriously lowered by the diffraction limit, when detecting an inherent molecular vibration of materials in a sample without staining the sample or adding fluorescent markers.

It is another object of the present invention to provide an imaging apparatus for infrared rays nonlinear molecular vibrational microscopy, which employs a far-field optical method which facilitates implementations in a diversity of application fields, instead of an access method using a near-field optical probe which is applied in the prior art, so as to secure the spatial resolution.

It is yet another object of the present invention to provide a new nonlinear optical four wave mixing spectroscopy as a core principle which can take advantage of measurement sensitivity caused by using the mid-IR laser beam source and also overcome a disadvantage in an aspect of spatial resolution.

It is yet another object of the present invention to provide a nonlinear signal collecting and processing optical system which can be practically realized in a microscopic imaging system.

Hereinafter, the present invention is described in detail.

To achieve the objects of the present invention, there has been provided an imaging apparatus for infrared nonlinear molecular vibrational microscopy, in which a microscopic image is obtained from a nonlinear molecular vibrational spectroscopic signal generated by that an infrared pump beam having a wavelength which is resonated with inherent molecular vibration of a material and a probe beam having a fixed short wavelength are combined to be focused and scanned spatially.

Therefore, the imaging apparatus for infrared nonlinear molecular vibrational microscopy comprises a pump beam source 10 for generating an infrared pump beam which excites medium molecules constituting the sample with a frequency in the molecular vibration band so as to be resonated with each other and thus forms molecular vibration coherence; a probe beam source 20 for generating a probe beam which detects the molecular coherence locally induced in a sample by the infrared pump beam; a beam combiner 30 which synchronizes temporally and overlaps spatially the pump beam and probe beam on the same path; a scanner 40 for two-dimensionally scanning the pump beam and the probe beam that are combined by the beam combiner 30; a first optical focusing system 50 for focusing the pump beam and the probe beam scanned by the scanner 40 on a local point within the sample; a first collecting optical system 60 for collecting signal light of which phase are shifted by that the input beams focused by the first optical focusing system 50 are interacted with the sample, and for collimating the collected light into a parallel beam; a first dichroic beam splitter 70 for removing the infrared pump beam out of the parallel beam formed by the first collecting optical system 60 and splitting the signal beam of which phase is shifted; a reference interferometer 80 for splitting a part of the probe beam out of the input beams scanned by the scanner 40 and generating a reference beam; an interferometric beam combiner 90 for combining the signal beam having the shifted phase and the reference beam; a photodetector 100 for detecting the intensity of a molecular vibrational interferometric signal from the signal beam and the reference beam that are combined by the interferometric beam combiner 90; and a data analyzer 110 for acquiring the interferometric signal detected by the photodetector 100 and generating and extracting a spectroscopic signal proportional to the degree of molecular vibrational coherence of the sample.

Further, the reference interferometer 80 is a Mach-Zehnder interferometer including a second dichroic beam splitter 81 for passing the pump beam out of the beams scanned by the scanner 40 and splitting a part of the probe beam, a second optical focusing system 82 for focusing the split probe beam, a second collecting optical system 83 for collecting the beam focused by the second optical focusing system 82 so as to form the parallel beam, and an optical path delay controller 84 for delaying an optical path of the parallel beam formed by the second collecting optical system 83, and the data analyzer 110 measures amplitude modulation of the interferometric signal to obtain phase difference between the signal beam having the modulated phase and the reference beam.

Further, the photodetector 100 uses a lock-in amplifier 101 in which a second harmonic frequency of the modulation in the molecular vibrational coherence is set as a reference frequency.

Further, the pump beam source is a wavelength-tunable beam source affording molecular vibrational resonance, realized by a DFG method (difference frequency generation) using a wavelength-tunable visible/near-infrared pulsed laser and a wavelength-fixed pulsed laser.

Further, the scanner 40 uses a galvano-mirror so as to scan the beam combined with the pump beam and probe beam at high speed on a two-dimensional plane.

Further, the photodetector 100 is a photomultiplier tube for detecting the optical signal with high amplification, or a high speed photodiode.

Further, the imaging apparatus of the present invention is used as a microscopic imaging apparatus.

DETAILED DESCRIPTION OF MAIN ELEMENTS

| | |
|---|---|
| 10: pump beam source | 11: amplitude modulator |
| 20: probe beam source | 30: beam combiner |
| 31: beam expander | 40: scanner |
| 50: first optical focusing system | |
| 60: first collecting optical system | |
| 70: first dichroic beam splitter | |
| 80: reference interferometer | |
| 81: second dichroic beam splitter | |
| 82: second optical focusing system | |
| 83: second colleceting optical system | |
| 84: optical path delay controller | |
| 90: interferometric beam combiner | |
| 100: photodetector | 101: lock-in amplifier |
| 110: data analyzer | |

BEST MODE FOR CARRYING OUT THE INVENTION

Practical and presently preferred embodiments of the present invention are illustrated as shown in the following Examples and Comparative Examples.

However, it will be appreciated that those skilled in the art, on consideration of this disclosure, may make modifications and improvements within the spirit and scope of the present invention.

Figure 1:
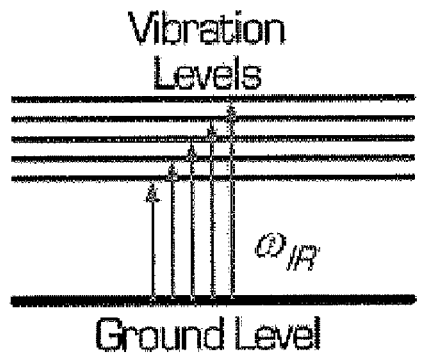
FIG. 1 is a diagram of a molecular vibrational transition showing a principle of measuring an infrared absorption spectroscopic signal.
Figure 2:
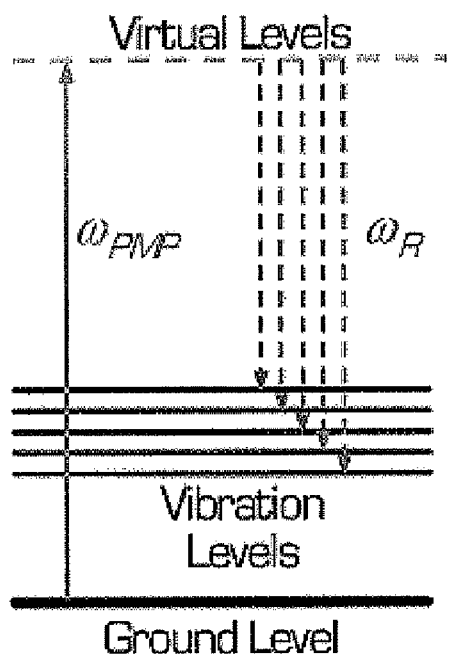
FIG. 2 is a diagram of a molecular vibrational transition showing a principle of generating a spontaneous Raman spectroscopic signal.
Figure 3:
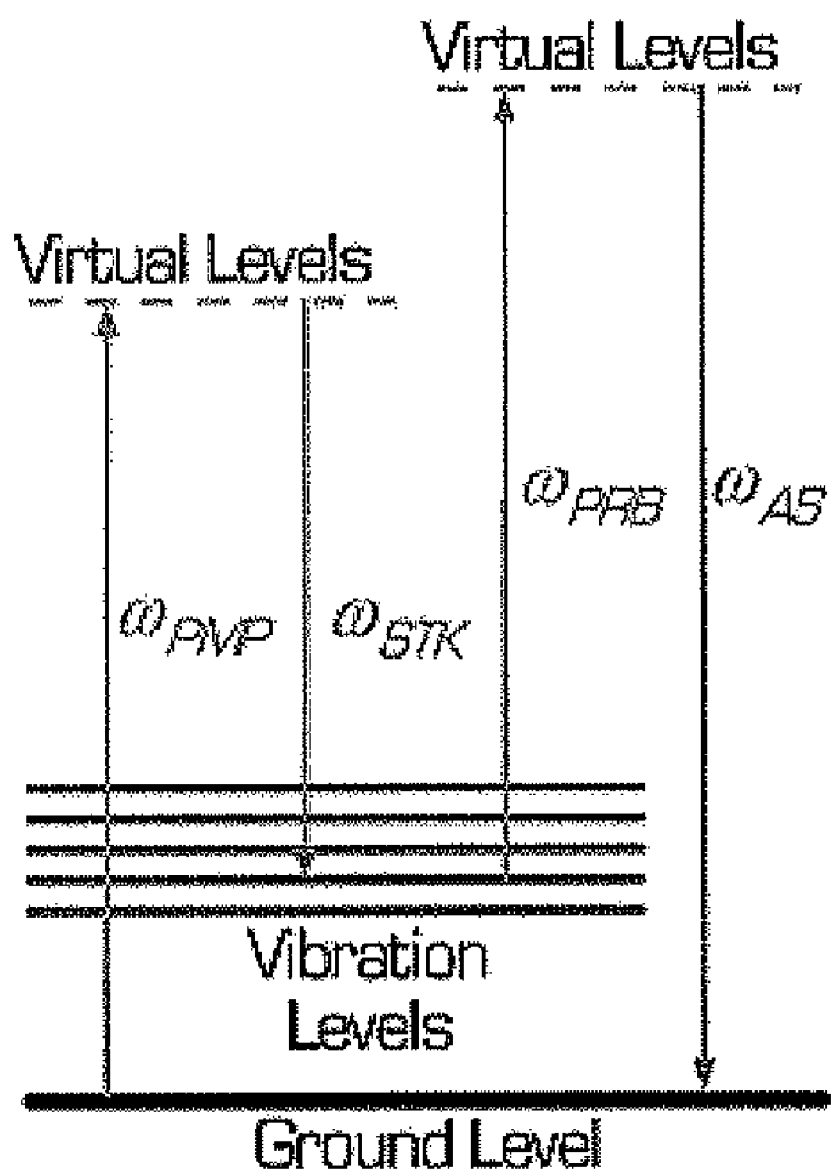
FIG. 3 is a diagram of a molecular vibrational transition showing a principle of generating a CARS nonlinear spectroscopic signal.
Figure 4:
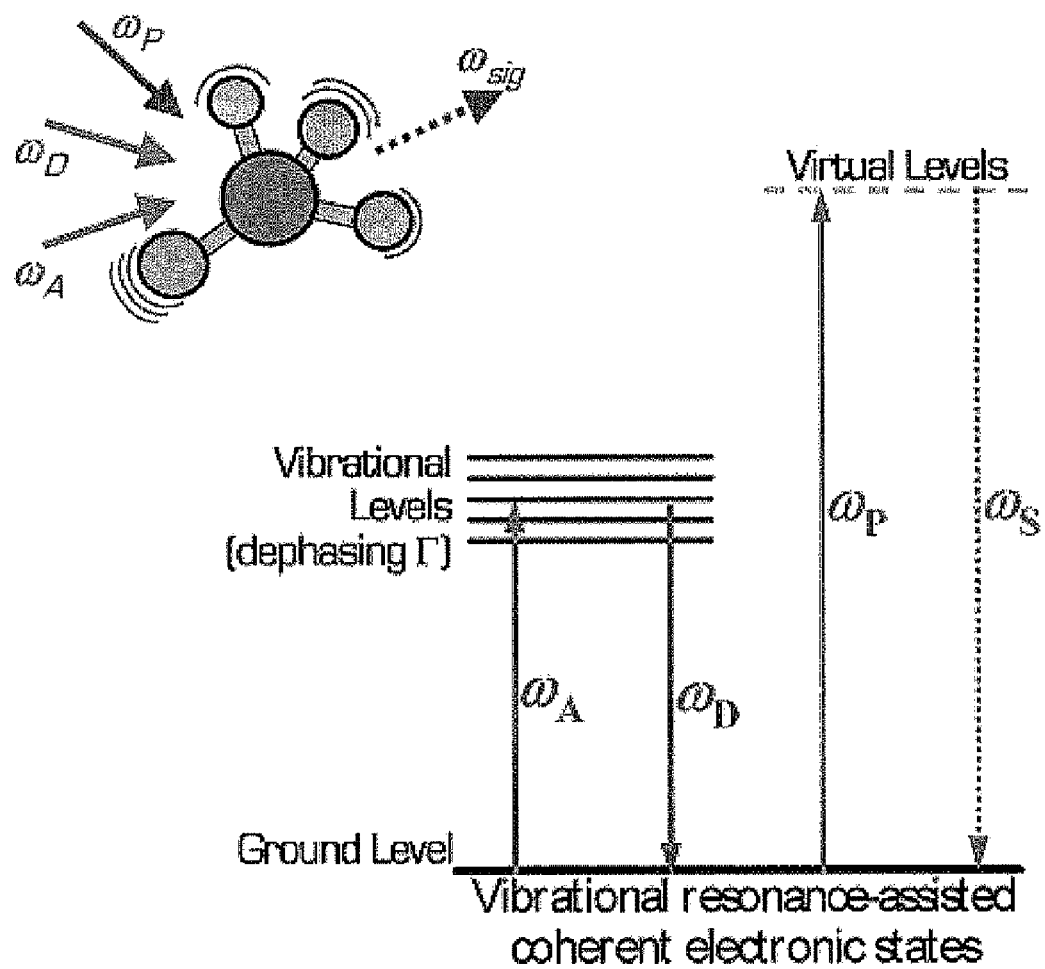
FIG. 4 is a diagram of laser-sample interaction energy level and transition which are proposed by an IR nonlinear molecular vibrational spectroscopy according to the present invention.

FIG. 4 is a diagram of laser-sample interaction energy level and transition which are proposed by an IR nonlinear molecular vibrational spectroscopy according the present invention.

In obtaining a selective spectroscopic signal with respect to a certain molecular vibration, if a laser having a frequency $\omega_A$ which resonates with the molecular vibration is incident to a sample, the laser is strongly absorbed. In this case, if a peak power of the laser is high enough, the molecule excited to a molecular vibrational energy level is resonantly de-excited back to a ground energy level. In this case, a frequency $\omega_D$ of the laser is the same as the absorbed frequency $\omega_A$, and thus the resonance absorption and the de-excitation to the ground level are occurred by that the substantially same laser provides coherence so as to cause the two actions in sequence. The sample returns to the ground energy level by the interaction with the laser, but an internal status of the sample is changed by the resonance transitions so as to have electronic coherence, which is different from its original status.

In a molecular aggregate having electronic coherence, a nonlinear refractive index change $\Delta n = n_2 I_{IR}$ proportional to an intensity of laser beam $I_{IR}$ and a material coefficient $n_2$ is induced additively to its original refractive index $n_0$. At this time, if a probe beam having a nonresonant frequency $\omega_P$ is incident on the sample, a signal, which has the same frequency $\omega_S$ as that of the probe beam and in which its phase is changed, is generated according to the nonlinear refractive index change.

Figure 5:
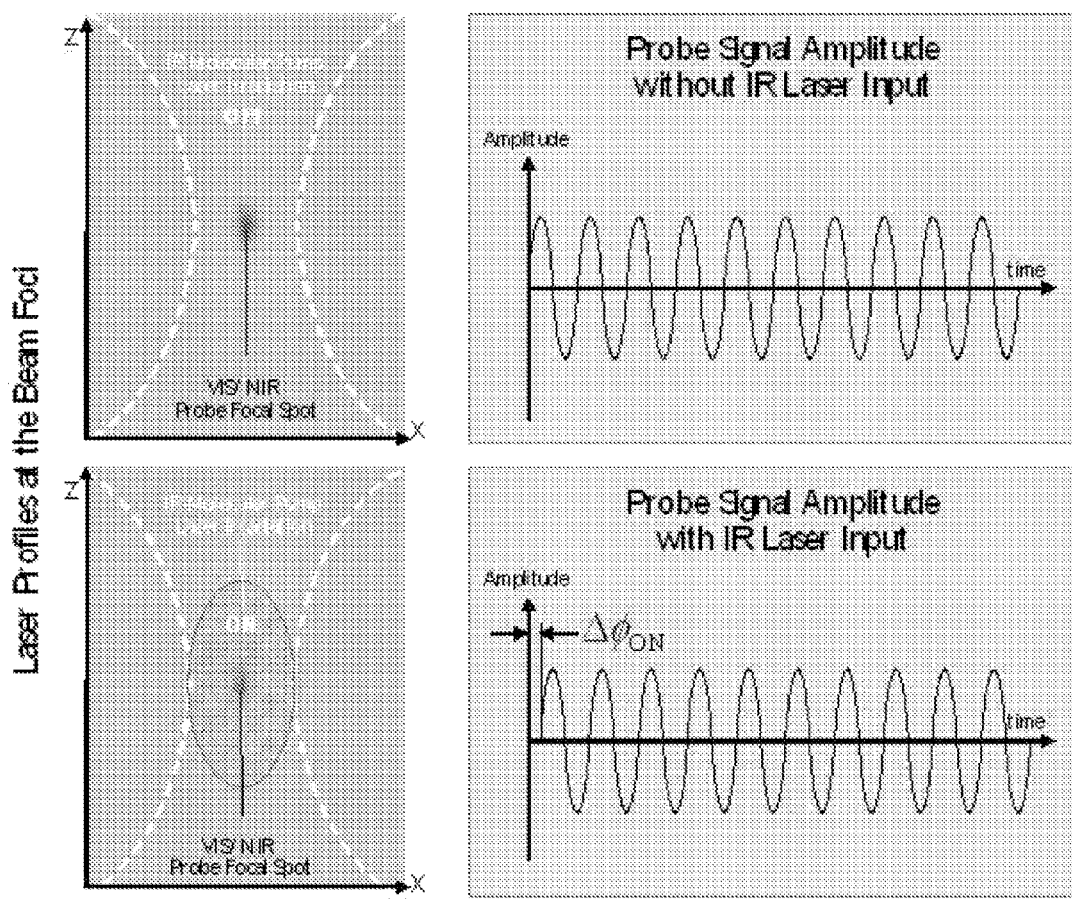
FIG. 5 is a schematic view showing a characteristic of measured physical quantity and spatial resolution, which is used for signal beam analysis in an imaging method for IR nonlinear molecular vibrational microscopy according to the present invention.

FIG. 5 is a schematic view showing a characteristic of measured physical quantity and spatial resolution, which is used for signal beam analysis in an imaging method for IR nonlinear molecular vibrational microscopy according to the present invention.

As described above, the spectroscopic signal of the present invention is generated when the beam ($\omega_A$, $\omega_D$) for inducing the resonance absorption in the infrared and the de-excitation back to the ground level is spatially coincident with the probe beam ($\omega_P$) of visible/near-infrared band for detecting the phase change. Each laser beam, which is used to generate the spectroscopic signal having a good spatial resolution in a microscope, is focused by objective lens and also localized at the same time.

In the case that there is no infrared pump beam ($\omega_A$, $\omega_D$) present, the probe beam of the visible/near-infrared band ($\omega_P$) is focused in the sample and then output as the signal beam having the initial frequency ($\omega_S=\omega_P$), which does not include any information of the molecular vibration. However, if the infrared laser beam ($\omega_A$, $\omega_D$) is made to interact with the molecular vibration of the sample, a signal beam, which has the same frequency ($\omega_S=\omega_P$) but with its phase changed by $\Delta\Phi$, can be obtained from the probe beam ($\omega_P$) focus in the sample. In other words, by measuring a magnitude of the phase change $\Delta\Phi$ of the signal beam between the case that the infrared laser beam ($\omega_A$, $\omega_D$) exists and the case that the infrared laser beam ($\omega_A$, $\omega_D$) does not exist, a concentration of chemical species whose molecular resonance resides distinctively at a specific frequency ($\omega_A=\omega_D$), can be quantified.

The spatial resolution of the nonlinear spectroscopic imaging apparatus according to the present invention has a different characteristic from other imaging apparatus used in a general laser microscope.

The theoretical limit of spatial resolution in a general optical image which is obtained by using the laser beam focused through an objective lens of a microscope is $\delta r=\lambda/2NA$ in the lateral direction (x-axis or y-axis), and $\delta z\approx 3\delta r$ in the longitudinal direction (z axis). Herein, the "$\lambda$" is a wavelength of the focused laser beam, and the "NA" is a numerical aperture of the objective lens which is determined by a refractive index of a medium and a focusing angle of the beam. A minimum focal spot size with infrared laser beams for inducing the resonance absorption and de-excitation, is limited to 2.5~18 μm, and the spatial resolution of the infrared microscope depends on this limit.

However, the present invention is characterized in that the spatial resolution is improved by using the inherent nonlinear optical phenomenon in which a plurality of laser beams having different wavelengths are made to interact with the sample. The nonlinear spectroscopic signal according to the present invention is generated from the light wave $E\omega_S$ of the frequency $\omega_s$ which is re-radiated by a third-order nonlinear polarization $P\omega_S^{(3)}=\chi^{(3)}E\omega_A E\omega_D^* E\omega_P$ of the sample. That is, the observation can be achieved only when the light waves $E\omega_A$, $E\omega_D$, and $E\omega_P$ having frequencies $\omega_A$, $\omega_D$, and $\omega_P$, respectively, are synchronously positioned at the same place within the sample having a third-order nonlinear susceptibility $\chi^{(3)}(\omega_S;\omega_A,-\omega_D,\omega_P)$.

In the case that each of the incident light waves is focused into a finite volume by the objective lens, the generation of signal beam is localized to a spot in which all of the light waves are overlapped spatially and the product of amplitudes becomes non-zero.

According to the present invention, the diffraction limit of the laser beam for inducing the resonance absorption ($E\omega_A$) and de-excitation ($E\omega_D$) of the infrared band is 2.5~18 μm, but a final spatial resolution of 0.3~0.7 μm is obtained by the probe beam ($E\omega_P$) of the visible/near-infrared band which can be tightly focused to a much smaller focal volume.

Figure 6:
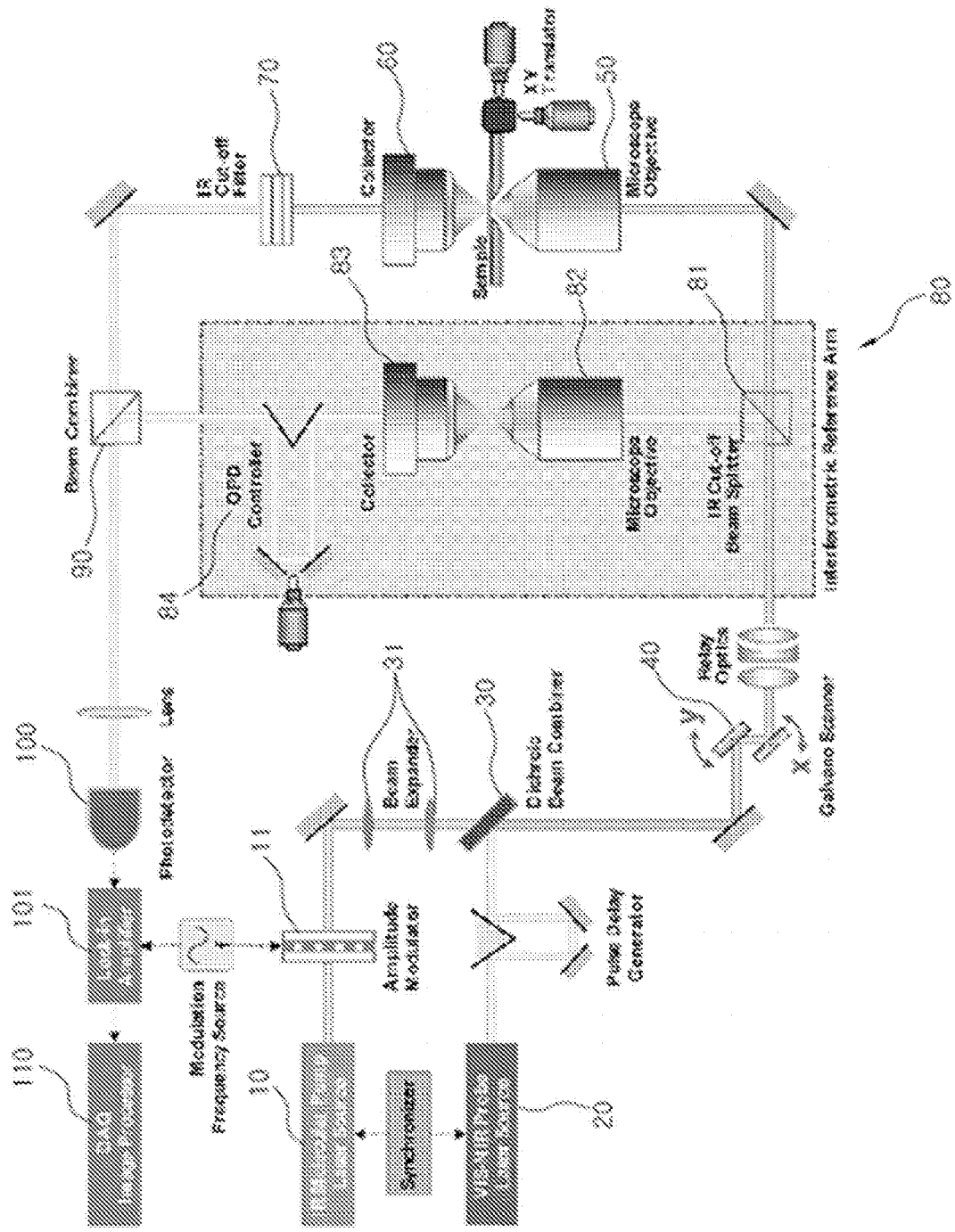
FIG. 6 is a view showing a construction of a microscopic imaging apparatus using the IR nonlinear molecular vibrational spectroscopy according to the present invention.

FIG. 6 is a view showing a construction of a microscopic imaging apparatus using the IR nonlinear molecular vibrational spectroscopy according to the present invention. The microscopic imaging apparatus is an example using an interferometer device which measures the phase change of the nonlinear optical signal and extracts the spectroscopic signal.

As shown in drawing, an imaging apparatus for infrared nonlinear molecular vibrational microscopy according to the present invention includes a pump beam source 10 for generating an infrared pump beam to excite medium molecules at a frequency in the molecular vibration band; a probe beam source 20 for generating a probe beam to detect the molecular vibration coherence induced by the infrared pump beam; a beam combiner 30 which synchronizes temporally and overlaps spatially the pump beam and probe beam on the same path; a scanner 40 for two-dimensionally scanning the combined pump beam and the probe beam; a first optical focusing system 50 for focusing the scanned pump beam and probe beam on a local point within the sample; a first collecting optical system 60 for collecting the beam of which phase is shifted by interaction with the sample and then collimating to a parallel beam; a first dichroic beam splitter 70 for removing the infrared pump beam out of the parallel beam and splitting out only the signal beam of which phase is shifted; a reference interferometer 80 for splitting a part of the probe beam out of the beams scanned by the scanner 40 and generating a reference beam; an interferometric beam combiner 90 for combining the signal beam having the shifted phase and the reference beam; a photodetector 100 for detecting the intensity of an interferometric signal between the signal beam and the reference beam; and a data analyzer 110 for acquiring the interferometric signal detected by the photodetector 100 and generating and extracting a spectroscopic signal proportional to the degree of molecular vibrational coherence of the sample.

The infrared pump beam source 10 functions to generate the infrared pump beam which excites medium molecules constituting the sample at a frequency in the molecular vibration band so as to be resonated with each other and thus forms molecular coherence state. The pump beam source 10 is a wavelength-tunable light source for providing two light wave components which cause an absorption (frequency $\omega_A$) resonated with the molecular vibration, and a ground level de-excitation (frequency $\omega_P$). Preferably, the pump beam source 10 outputs a repetitive pulse having a high peak power.

The probe beam source 20 functions to generate the probe beam for detecting the coherence state which is locally induced in the sample by the infrared pump beam. The probe beam source 20 generates the probe beam having a frequency ($\omega_P$) in a visible or IR band, and also generates a signal beam (frequency $\omega_S=\omega_P$) while passing through a molecular aggregate with molecular coherence.

At this time, the infrared pump beam source 10 and visible pump beam source 20 use a synchronizer for performing pulse timing synchronization with high precision and an optical pulse delay generator, so as to output a temporally overlapped ultrashort pulse train.

The infrared pump beam and visible pump beam which are temporally synchronized are spatially overlapped on the same axis and then combined by an additional device for matching their beam sizes. The additional device includes a beam expander 31 which is positioned either in a pump or in a probe beam path, and a beam combiner 30 for synchronizing and overlapping the pump beam and probe beam temporally and spatially on the same axis.

The beam combiner 30 is a dichroic beam combiner in which the pump beam and the probe beam in different frequency bands have opposite characteristics in reflection and transmission.

The pump beam and probe beam combined by the beam combiner 30 are two-dimensionally scanned by the scanner 40 so as to obtain a microscopic image, and directed to a microscope objective lens, i.e., the first optical focusing system 50 which is positioned at the front side of the sample, and then focused on a local point within the sample.

The first collecting optical system 60 collects signal beam of which phase are shifted by that the beams focused by the first optical focusing system 50 are interacted with the sample and forms a parallel beam;

After the beam is collimated into the parallel beam by the first collecting optical system 60, the beam passes through the first dichroic beam splitter 70 as an IR cut-off filter for removing the infrared pump beam. Therefore, only the probe beam having the shifted phase is split out.

The reference interferometer (interferometric reference arm) 80 splits a part of the probe beam out of the beams scanned by the scanner 40, and generates the reference beam. The reference beam is crucial in quantitatively analyzing the molecular vibrational coherence of the sample by using a phase change in the signal beam.

Preferably, the reference interferometer 80 is a Mach-Zehnder interferometer including a second dichroic beam splitter 81 for filtering the pump beam out of the beams scanned by the scanner 40 and splitting a part of the probe beam, a second optical focusing system 82 for focusing the split probe beam, a second collecting optical system 83 for collecting the beam focused by the second optical focusing system 82 so as to form the parallel beam, and an optical path delay controller 84 for delaying an optical path of the parallel beam formed by the second collecting optical system 83.

The signal beam having the shifted phase and split by the first dichroic beam splitter and the reference beam generated by the reference interferometer 80 are combined by the interferometric beam combiner 90.

The photodetector 100 detects the intensity of the molecular vibrational interferometric signal between the signal beam and the reference beam which are combined by the interferometric beam combiner 90.

The data analyzer 110 acquires the interferometric signal detected by the photodetector 100 and generates and extracts the spectroscopic signal proportional to the degree of molecular vibrational coherence of the sample. At this time, the data analyzer 110 measures amplitude modulation of the interferometric signal to obtain phase difference between the signal beam having the modulated phase and the reference beam.

As described above, the present invention includes the optical microscope arrangement and the reference interferometer 80 in the Mach-Zehnder-type configuration.

The reference interferometer 80 begins with the second dichroic beam splitter 81 inserted in the optical path through which the combined pump beam and probe beam are propagating. A part of the probe beam reflected by the second dichroic beam splitter 81 is passed through a microscope objective lens, i.e., the second optical focusing system 82 and the second collecting optical system 83, in which the sample is absent, and then arrives at the interferometric beam combiner 90 via the optical path delay controller 84.

When the two separate probe beams which are made to pass through the microscope path and the reference arm path are combined by the interferometric beam combiner 90, the interferometric signal beam is then generated. The intensity $I_{int}$ of an interferometric signal beam can be determined with the intensity $I_{sig}$ of the signal beam passing through the microscope path, the intensity $I_{ref}$ of the reference beam, and the phase change $\Delta\Phi$ between the two optical paths, as follows:

$$I_{int} = I_{sig} + I_{ref} + 2\sqrt{I_{sig}I_{ref}} \cos[\Delta\phi(\vec{x};t)]$$

The phase change $\Delta\Phi$ is caused by the length difference between the two optical paths with spatial nonuniformity taken into account as a function of position ($\vec{x}$) within the sample. The phase change $\Delta\Phi$ can also be modulated by temporal changes in the sample status.

If the field amplitude $E_{IR}$ of the infrared pump beam is modulated at angular frequency $\omega_m$ by using an amplitude modulator 11 which is positioned at the front side of the infrared pump beam source 10, the intensity $I_{IR}$ of the infrared pump beam which induces a nonlinear refractive index change (Kerr effect) $\Delta n = n_2 I_{IR}$ in the sample is then modulated as follows;

$$I_{Kerr} = I_{IR}\cos^2\omega_m t = I_{IR}\left[\frac{1+\cos 2\omega_m t}{2}\right]$$

Therefore, assuming that the nonlinear phase change $\Delta\Phi$ of the sample is proportional to the intensity $I_{Kerr}$ of the modulated infrared pump beam and the coefficient ($k(\vec{x})$) corresponding to the spatial characteristic of a nonuniform sample, a phase difference between the optical paths in the interferometer device can be expressed as follows:

$$\Delta\phi(\vec{x};t) = k(\vec{x})\cdot I_{IR}\left[\frac{1+\cos 2\omega_m t}{2}\right] + \Delta\phi_0(\vec{x})$$

Here, the $\Delta\phi_0(\vec{x})$ indicates a phase difference term irrelevant to the infrared pump beam modulation. A total phase difference $\Delta\Phi(\vec{x};t)$ of the interferometer device can be divided into an AC component $\Delta\phi_{AC}(\vec{x})$ and a DC component $\Delta\phi_{DC}(\vec{x})$, and each of the components reads as follows:

$$\Delta\phi_{AC}(\vec{x}) = \frac{k(\vec{x})\cdot I_{IR}}{2}$$

$$\Delta\phi_{DC}(\vec{x}) = \frac{k(\vec{x})\cdot I_{IR}}{2} + \Delta\phi_0(\vec{x})$$

Figure 7:
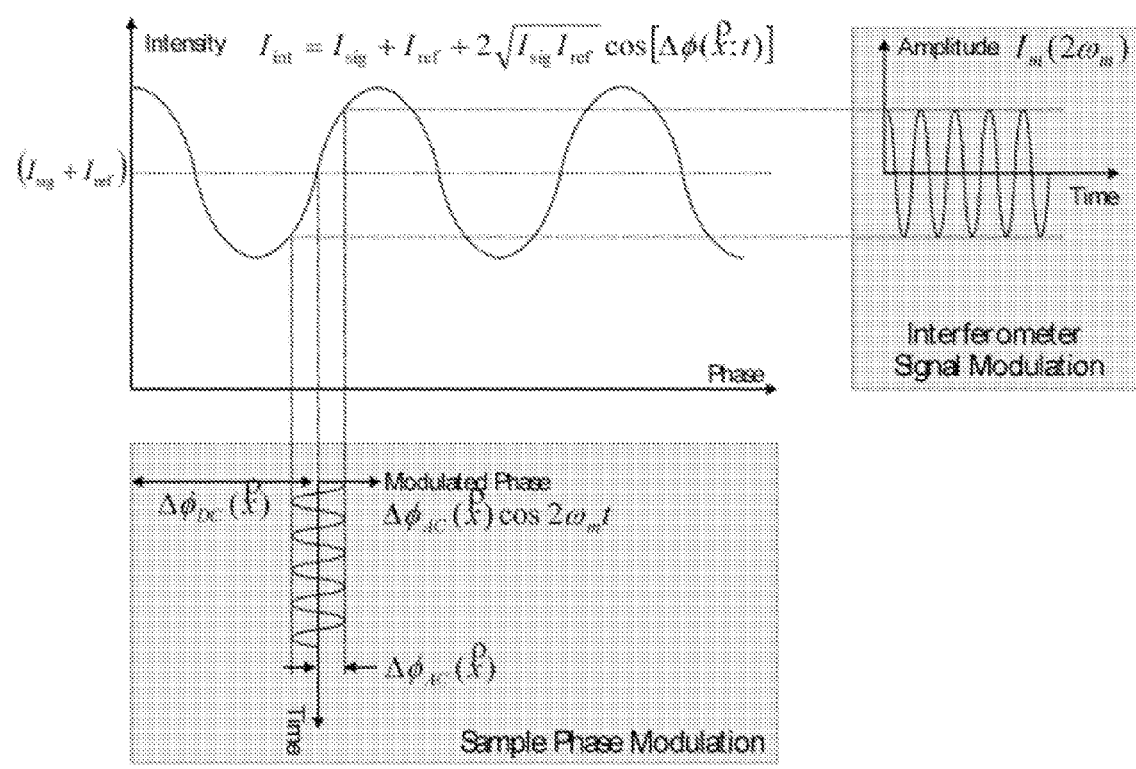
FIG. 7 is a schematic view showing the principle of interferometric signal generation in the optical interferometer measuring the modulation of molecular vibrational coherence.

Therefore, the intensity of the modulated interferometric signal beam follows a behavior depicted in FIG. 7.

FIG. 7 is a schematic view showing the principle of interferometric signal generation in the presence of amplitude modulation of an infrared pump laser input.

Intensity of the interferometric signal beam with the modulated phase difference $\Delta\phi(\vec{x};t)$ can be described as:

$$I_m \propto \cos[\Delta\phi_{AC}(\vec{x})\cos 2\omega_m t + \Delta\phi_{DC}(\vec{x})].$$

When the DC component of phase difference $\Delta\phi_{DC}(\vec{x})$ can be set to $$\Delta\phi_{DC}(\vec{x}) \rightarrow \frac{3\pi}{2}$$

by precisely adjusting the optical path delay controller in the interferometric reference arm, the interferometric signal intensity is given by:

$$I_m \propto \sin[\Delta\phi_{AC}(\vec{x})\cos 2\omega_m t]$$

The final output of the interferometric signal beam of the present invention is focused onto a high-sensitivity and high-speed photodetector 100 so that a photocurrent measurement is performed. Here, it is preferable that the photodetector 100 uses a lock-in amplifier 101 in which a second harmonic of the amplitude modulation frequency of the molecular vibration excitation is set as a reference frequency.

If lock-in amplification with respect to the second harmonic of amplitude modulation frequency $f = \omega_m/2\pi$ of the pump beam is performed, the lock-in output for the interferometric signal is then expressed as follows:

$$I_m(2\omega_m) \propto 2J_1(\Delta\phi_{AC}(\vec{x}))\cos 2\omega_m t.$$

Finally, the amplitude component $2J_1(\Delta\phi_{AC}(\vec{x}))$ is used as a molecular vibrational detection signal. Herein, $J_1$ denotes the first-order Bessel function.

The nonlinear IR molecular vibrational microscopic image is obtained by measuring the molecular vibrational detection signal as a function of the spatial position ($\vec{x}$). To this end, the scanner 40 is used, which can three-dimensionally change the focal spot position of the laser beam in the sample.

Preferably, the scanner 40 of the present invention uses a motorized scanner which mechanically translates the position of the sample relative to a fixed laser focus on the xy-plane and in the z-axial direction, or deflects the beam combined with the pump beam and probe beam at a high speed on a two dimensional plane by a galvano mirror.

Preferably, the imaging apparatus for infrared nonlinear molecular vibrational microscopy according to the present invention is used in a high resolution microscope.

According to the present invention, since a nonlinear optical four-wave mixing spectroscopy is employed in the infrared molecular vibrational imaging system, it is possible to provide a far-field laser microscope with excellent detection sensitivity and spatial resolution.

INDUSTRIAL APPLICABILITY

According to the present invention, as described above, by using the infrared pump beam which is strongly resonated with the molecular vibration, it is possible to solve the problem of low detection sensitivity in the conventional molecular vibrational microscope based on spontaneous Raman scattering and coherent anti-Stokes Raman scattering (CARS) Furthermore, by extracting the nonlinear molecular vibration spectroscopic signal through the probe beam having a short wavelength, it is possible to solve the problem of unsatisfactory spatial resolution of the conventional linear IR absorption molecular vibrational microscope, there obtaining an excellent resolution. Furthermore, the present invention can contribute to remarkably improve the image acquisition speed and the image quality in the field of molecular vibrational microscope.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. An imaging apparatus for infrared nonlinear molecular vibrational microscopy, comprising:
   a pump beam source for generating an infrared pump beam which excites medium molecules constituting a sample with a frequency in molecular vibration bands so as to be resonated with each other and thus forms a molecular vibration coherence;
   a probe beam source for generating a probe beam which detects the molecular coherence of a sample locally induced by the infrared pump beam;
   a beam combiner which synchronizes temporally and overlaps spatially the pump beam and probe beam on the same path;
   a scanner for two-dimensionally scanning the pump beam and the probe beam combined by the beam combiner;
   a first optical focusing system for focusing the pump beam and the probe beam scanned by the scanner on a local point within the sample;
   a first collecting optical system for collecting beams of which phase are shifted by the beams focused by the first optical focusing system are interacted with the sample, and for collimating the collected light into a parallel beam;
   a first dichroic beam splitter for removing the infrared pump beam out of the parallel beam formed by the first collecting optical system and splitting the signal beam of which phase is shifted;
   a reference interferometer for splitting a part of the probe beam out of the beams scanned by the scanner and generating a reference beam;
   an interferometric beam combiner for combining the signal beam having the shifted phase and the reference beam;
   a photodetector for detecting the intensity of a molecular vibrational interferometric signal between the signal beam and the reference beam which are combined by the interferometric beam combiner; and
   a data analyzer for acquiring the interferometric signal detected by the photodetector and generating and extracting a spectroscopic signal proportional to the degree of molecular vibrational coherence of the sample,
   wherein the reference interferometer is a Mach-Zehnder interferometer including a second dichroic beam splitter for passing the pump beam out of the beams scanned by the scanner and splitting a part of the probe beam, a second optical focusing system for focusing the split probe beam, a second collecting optical system for collecting the beam focused by the second optical focusing system so as to form the parallel beam, and an optical path delay controller for delaying an optical path of the parallel beam formed by the second collecting optical system, and the data analyzer measures amplitude modulation of the interferometric signal to obtain phase difference between the signal beam having the modulated phase and the reference beam.

2. The imaging apparatus as set forth in claim 1, wherein the photodetector uses a lock-in amplifier in which the second harmonic of the modulation frequency of the molecular vibrational signal is set as a reference frequency.

* * * * *